United States Patent [19]
Jones

[11] Patent Number: 5,267,668
[45] Date of Patent: Dec. 7, 1993

[54] CHILD RESISTANT STORAGE AND DISPOSAL BOX

[76] Inventor: Hedwig E. Jones, 3519 Gemini Ct., Concord, Calif. 94519

[21] Appl. No.: 70,865

[22] Filed: Jun. 1, 1993

[51] Int. Cl.$^5$ ............................................. B65D 1/24
[52] U.S. Cl. ................................. 220/326; 220/908; 220/523; 206/363
[58] Field of Search ............... 220/326, 323, 523, 524, 220/526, 908; 206/363

[56] References Cited

U.S. PATENT DOCUMENTS

| | | |
|---|---|---|
| 2,809,766 | 10/1957 | Anderson ............................ 220/326 |
| 3,113,817 | 12/1963 | Emel ................................... 220/523 |
| 3,175,853 | 3/1965 | Gilbertson ........................... 220/326 |
| 3,704,395 | 11/1972 | Hamer et al. ....................... 220/326 |
| 4,344,646 | 8/1982 | Michel ................................. 220/326 |
| 4,520,921 | 6/1985 | Vissing ................................ 220/326 |

*Primary Examiner*—Joseph Man-Fu Moy

[57] ABSTRACT

A child resistant storage box for medical supplies for one patient, in-home care, incorporating a disposal unit which can be separately closed off before final disposal comprises a box made of rigid plastic having a cover and a container portions, tabs of slightly flexible plastic attached to the inside rim of the cover on either side, circular pieces of rigid plastic or rounds, integrally bonded to the tabs and of a size and thickness to complement circular openings in the two sides of the container.

4 Claims, 1 Drawing Sheet

CHILD RESISTANT STORAGE AND DISPOSAL BOX

BACKGROUND OF THE INVENTION

1. Field of the Invention

The invention relates generally to a storage box for medical supplies which are used in a home-care setting. Built into the box is a disposal section for sharp objects such as used needles and syringes. It has a child resistant opening mechanism and is for one-patient-use only.

2. Description of the Prior Art

In-home care for patients is a rapidly expanding field, as it cuts health care costs. More and more complicated procedures are now done by visiting nurses in the patient's home, from I.V. drug delivery to wound care to tube feedings. These procedures require supplies to be on hand which need to be accessible both to the nurse and the patient's family, who often take part in the care. Supplies are at present left in a card-board box or a similar receptacle where they are accessible to young children. Similarly, children have access to any sharps disposal units left standing in the open and by no means impossible of penetration.

This invention will provide a safe, covered place for both supplies and disposal. The opening mechanism requires the sort of co-ordination in movements which young children generally lack. The result is a child-resistant box which will fill a real need in the home-care field.

SUMMARY OF THE INVENTION

The invention consists of a portable box made of rigid plastic and corresponds in shape and size roughly to an attaché case, but this may be varied to fit individual needs. A rimmed, flexibly attached cover provides child resistant closing means. The inside of the box is divided into compartments for the storage of medical supplies. One compartment forms a disposal unit. It has a fixed top with a slot to drop sharp objects into it. Before final disposal, this compartment can be further secured by snapping a separate lid over it.

DESCRIPTION OF THE PREFERRED EMBODIMENT

Figure 1:
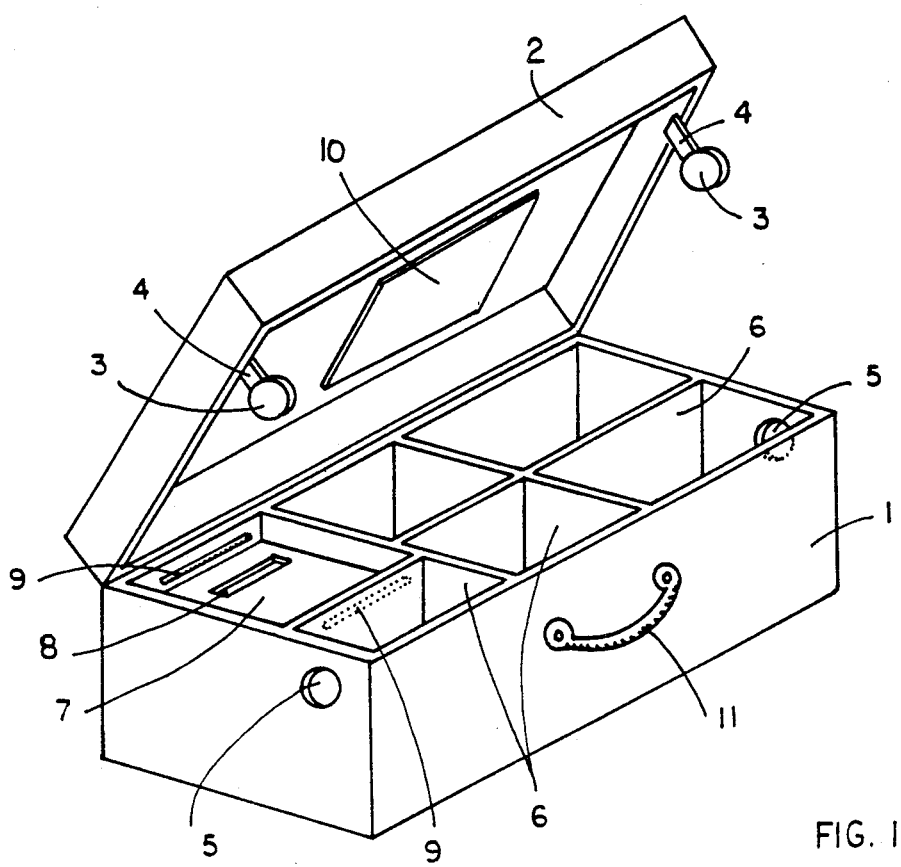
FIG. 1 is an elevational view of one embodiment of the invention. The partly open cover shows the closing means as well as the inside compartments of the box, including the disposal unit.

Referring to FIG. 1, an embodiment of the invention is shown. A box 1, or case of rigid plastic has a flexibly attached, rimmed cover 2 and a carry handle 11. To secure the box 1 from child tampering, a child-resistant opening and closing device is provided: The box 1 shows circular openings 5 in both sides near the top. Slightly flexible tabs 4 are attached to the inside rim of the cover 2 on either side. The tabs 4 bear circular pieces of rigid plastic, or rounds 3, which are integrally bonded to them. The rounds 3 correspond in size and thickness to the circular openings 5 in the box 1. When closing the box 1, the rounds 3 will snap into the circular openings 5, locking the cover 2 in place. The inside of the box 1 shows dividing walls 6 to create a multiplicity of compartments for the storage of medical supplies. One of the compartments is transformed into a disposal unit by adding a fixed top 7 with a narrow slot 8 in it. Here sharp objects can be disposed of safely. When nursing care of a patient is terminated, the disposal unit can be further secured by closing it off with a separate lid 10, which is removably attached to the inside of cover 2 until needed. The separate lid 10 is placed over the top 7 of the disposal unit and will come to rest on the rounded bars 9 on either end of the disposal compartment above the top 7. The separate lid 10 is flexible and when pushed downwards in the center, will snap over the bars 9 and come to rest on the top 7, closing off the slot 8. The bars 9 will prevent the lid 10 from coming off again. Now the whole box 1 is ready for final disposal.

Figure 2:
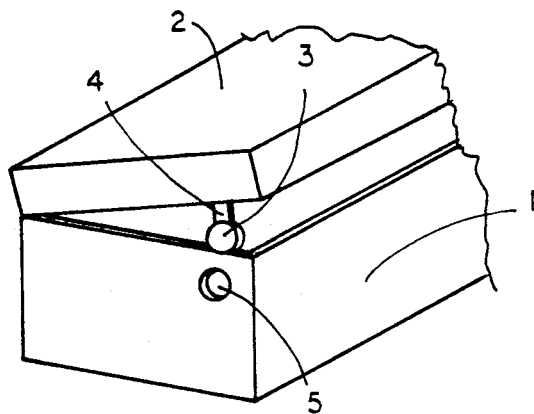
FIG. 2 is a partial view of the invention, showing the cover lowered and the box ready to be closed.

Referring to FIG. 2, the method of closing the box 1 is shown. The cover 2 is lowered, until the rounds 3 attached to the tabs 4 come to rest on the sides of the box 1. By pushing both rounds 3 inwards, the cover 2 will close completely and the rounds 3 will snap into the holes 5 in the sides of the box 1. To open the box 1 again, the rounds 3 are pushed inwards with the index fingers, while the thumbs push simultaneously upwards on the cover 2. This requires a degree of co-ordination which is difficult to achieve for small children.

Figure 3:
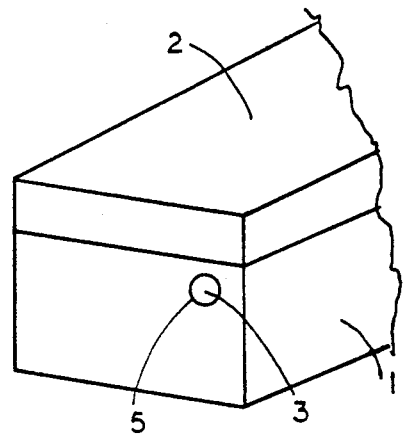
FIG. 3 is another partial view of the invention, showing the box after it is closed, leaving the outer aspect smooth, with no protrusions.

Referring to FIG. 3, the closed box 1 is shown. Only the outline of the openings 5 show, leaving the outer aspect of the box 1 smooth, without knobs or buttons protruding which invite investigation. The opening mechanism is difficult for a young child to figure out or to activate, which protects the contents of the box 1.

Although an embodiment of the invention is illustrated in the drawings and previously described in detail, this invention encompasses any design and relationship of components which will function in a similar manner and which will provide the equivalent results.

I claim:

1. A child-resistant storage and disposal box comprising:
   (a) a box made of rigid plastic, having a bottom, a front, a back and two sides, defining an open top;
   (b) small, circular openings in the two sides, near their top;
   (c) a flexibly attached, rimmed cover of rigid plastic, complementing the open top;
   (d) tabs of slightly flexible plastic attached to the inside rim of the cover on either side;
   (e) circular pieces of rigid plastic or rounds, integrally bonded to the tabs and of a size and thickness to complement the circular openings in the two sides;
   (f) dividing walls inside the box, creating a multiplicity of compartments;
   (g) a fixed top closing off one of the compartments at a distance below the top of the walls defining it, for use as a disposal unit;
   (h) rounded bars on two opposing walls of the same compartment, above the fixed top;
   (i) a separate lid of flexible plastic, complementing the top of the disposal unit and removably attached to the inside cover of the box;
   (j) a carry handle attached to the front of the box.

2. A storage and disposal box as recited in claim 1, in which the flexibly attached cover can be closed down, when the rounds bonded to the tabs on the cover will come to rest on the sides of the box and when pushed inwards, will snap into the circular openings in the sides of the box.

3. A storage and disposal box as recited in claim 2, in which the fixed top of the disposal unit shows a narrow slot for the disposal of sharp objects.

4. A storage and disposal box as recited in claim 3, in which the separate lid can be put on top of the rounded bars above the disposal unit and by pressing down in the center be made to snap downwards over the bars, closing off the disposal unit.

* * * * *